(12) United States Patent
Hauenstein

(10) Patent No.: US 7,906,134 B2
(45) Date of Patent: Mar. 15, 2011

(54) ROOM TEMPERATURE-CURABLE POLYMERS

(75) Inventor: Dale Hauenstein, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 831 days.

(21) Appl. No.: 11/314,372

(22) Filed: Dec. 21, 2005

(65) Prior Publication Data

US 2007/0141104 A1 Jun. 21, 2007

(51) Int. Cl.
*A61F 2/00* (2006.01)
(52) U.S. Cl. ........................................ 424/423
(58) Field of Classification Search ......................... None
See application file for complete search history.

(56) References Cited

U.S. PATENT DOCUMENTS

| | | | |
|---|---|---|---|
| 4,742,092 A * | 5/1988 | Inoue et al. | 522/27 |
| 5,648,442 A | 7/1997 | Bowers et al. | |
| 5,705,583 A | 1/1998 | Bowers et al. | |
| 5,969,075 A | 10/1999 | Inoue | |
| 6,015,815 A | 1/2000 | Mollison | |
| 6,090,901 A | 7/2000 | Bowers et al. | |
| 6,284,854 B1 | 9/2001 | Bowers et al. | |
| 2005/0208093 A1 | 9/2005 | Glauser et al. | |

FOREIGN PATENT DOCUMENTS

| | | |
|---|---|---|
| EP | 0604851 A1 | 7/1994 |
| WO | WO 03/022324 | 3/2003 |

OTHER PUBLICATIONS

Lewis, A.L., Z.L. Cumming, H.H. Goreish, L.C. Kirkwood, L.A. Tolhurst, and P.W. Stratford. 2001. Crosslinkable coatings from phosphorylcholine-based polymers. Biomaterials. 22:99-111.
Lewis, A.L., P.D. Hughes, L.C. Kirkwood, S.W. Leppard, R.P. Redman, L.A. Tolhurst, and P.W. Stratford. 2000. Synthesis and characterisation of phosphorylcholine-based polymers useful for coating blood filtration devices. Biomaterials. 21:1847-59.
International Search Report for PCT/US06/62066, filed Dec. 14, 2006, mailed Oct. 17, 2007, 7 pgs.

* cited by examiner

*Primary Examiner* — Michael G Hartley
*Assistant Examiner* — Paul Dickinson
(74) *Attorney, Agent, or Firm* — Squire Sanders & Dempsey (US) LLP

(57) ABSTRACT

Methods of making room temperature-curable polymers. Reactants include siloxane-terminated polymers and silanols. The reactants are mixed, and the polymerization allowed to proceed in air at room temperature. The polymers are exceptionally useful because they allow for the incorporation into the polymers themselves of one or more therapeutic compounds. Thus, medical devices from which controlled drug release is desirable (for either local or systemic delivery) can be coated with therapeutic compound-containing polymers of the invention. In a preferred embodiment, a polymer of poly($MPC_w:LAM_x:HPMA_y:TSMA_z$) where w, x, y, and z represent the molar ratios of monomers used in the feed for preparing the polymer; MPC represents the unit 2-methacryoyloxyethylphosphorylcholine, LMA represents the unit lauryl methacrylate, HPMA represents the unit 2-hydroxypropyl methacrylate, and TSMA represents the unit 3-trimethoxysilylpropyl methacrylate is reacted with polydimethylsiloxane. In another preferred embodiment, a therapeutic compound is incorporated into the polymer, such as dexamethasone.

42 Claims, No Drawings

ROOM TEMPERATURE-CURABLE POLYMERS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable.

TECHNICAL FIELD

The present invention relates to compositions and methods to produce room temperature curable polymers, such as phosphorylcholine polymers. In one embodiment, a phosphorylcholine polymer is formed, from which a drug can be released at a controlled rate. Such a composition eliminates the need for excessive processing conditions, such as heat and γ radiation, and permits further use of the coating in applications that had previously been restricted.

BACKGROUND OF THE INVENTION

Introduction

Polymer coatings enhance the capabilities of many of today's medical devices. Some coatings add such properties as lubricity, biocompatibility, and anti-microbial properties to device surfaces. Other coatings can be used to deliver therapeutic compounds from devices, or make implanted devices more easily detected by imaging systems.

For coatings designed to deliver therapeutic compounds, the compounds are usually coated on to the surface of the polymer coating. To be embedded in the polymer itself, which would lend more control to therapeutic compound release, the compound is incorporated during the polymerization reaction. However, most polymerization reaction conditions are incompatible with the therapeutic compounds maintaining their pharmacological attributes. Especially damaging reaction conditions include heat and γ irradiation.

Coating a device, such as a medical device (e.g., a stent), uses processes where a polymer is dissolved in a solvent, such as ethanol. The device is coated with the polymer using an appropriate method, such as dipping the device into the polymer solution or by spraying the polymer solution onto the device. Upon coating, the device is usually subjected to a curing condition, such as heat and γ irradiation. A drug can be loaded onto the coating by dipping or spraying techniques after the heat and γ irradiation steps, but results in the drug remaining primarily on the surface of the polymer.

For examples of conventional heat or γ irradiation cures, see (Bowers et al., 1997; Bowers et al, 2000; Bowers et al., 2001; Bowers et al., 1998). The BiodivYsio™ stent (product of Biocompatibles UK Ltd, Farnham, Surrey; UK) is coated with a biocompatible phosphorylcholine (PC) polymer comprised of 2-methacryloyloxyethyl phosphorylcholine, lauryl methacrylate, 2-hydroxypropyl methacrylate and 3-trimethoxysilylpropyl methacrylate monomers. The coating, once applied, is cured with heat, typically 70° C. for a minimum of 4 hours, and γ irradiated to insure proper material characteristics, such as cross-link density. These conditions, however, severely restrict the uses of the polymer coating to contain sensitive materials. Examples of some sensitive materials (other than therapeutic compounds) include nylon 11 that cannot tolerate high temperatures before undergoing a glass transition (between 45-48° C.); and polytetrafluoroethylene, which suffers deterioration of its mechanical properties when exposed to γ irradiation. These materials are used in the construction of some embolic filter devices. In addition, the efficacy of drug that is loaded within the PC polymer matrix for controlled local delivery is often compromised by excessive processing conditions. Such cures are also taught throughout the literature. For example, Lewis et al. (2001) describe preparation and characterization of phosphorylcholine (PC) polymers that includes the use of heat and γ irradiation to cross-link trimethoxysilyl groups of 3-trimethoxysilylpropyl methacrylate monomers (a pendant group extending from the backbone of a PC polymer) (Lewis et al., 2001). The synthesis and characterization for copolymers of 2-methacryloyloxyethylphosphorylcholine (MPC) and lauryl methacrylate (LMA), which do not contain 3-trimethoxysilylpropyl methacrylate monomer and therefore cannot undergo cross-linking through trimethoxysilyl groups has also been described (Lewis et al., 2000).

Other methacrylate copolymers incorporating the 3-trimethoxysilylpropyl methacrylate monomer for curable coating systems have been used in other industries, such as the automotive industry for automotive refinishing (automotive topcoats) where a final clear coating is applied over a pigmented basecoat. These systems, however, typically require the addition of a catalyst (such as tetrabutyltitanate or dibutyltin dilaurate), as well as excessive heat for an extended period of time to provide proper cure—all of which can restrict the incorporation of suitable therapeutic compounds to those that are not degraded or otherwise adversely affected (e.g., loss of therapeutic activity) by the curing steps.

Finally, a moisture curable sealant composition where alkoxysilane functionality can be grafted onto an acrylic polymer backbone to produce an alkoxysilane-functionalized acrylic polymer which can then be reacted with a reactive silanol solution containing reactive silicone (and, optionally, a silane cross-linker) to form a silicone-acrylic hydride polymer network through a silanol-alkoxysilane condensation reaction has been described (Hernandez, 1994). The resulting cross-linked silicone-acrylic hybrid polymer can be used in sealant, adhesive or coating compositions.

BRIEF DESCRIPTION OF THE DRAWINGS

Not applicable

SUMMARY OF THE INVENTION

In a first aspect, the invention is directed to the preparation of compositions, which may or may not further comprise at least one therapeutic compound, comprising a molecule of formula IV:

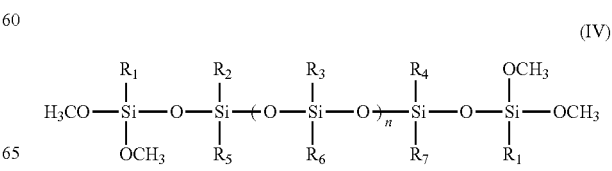

wherein the molecule of formula IV is made by reacting a molecule of formula I:

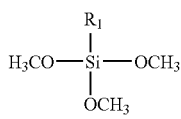

(I)

with a molecule of formula II:

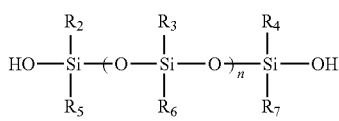

(II)

wherein $R_1$ comprises a polymer, the polymer containing at least one selected from the group consisting of an acyloxy, alkenyl, alkoxyl, alkyl, alkylcycloalkenyl, alkylcycloalkyl, alkenylcycloalkyl, alkynyl, amino, aralkyl, aryl, cycloalkenyl, cycloalkenylalkyl, cycloalkyl, cycloalkylalkyl, cycloalkylcycloalkyl, halogen, heterocycle, heterocyclic, ketone, N-acylamino, N-containing heterocycle; saturated cyclic, partially saturated cyclic, unsaturated cyclic; saturated ring structure, partially saturated ring structure, unsaturated ring structure, and combinations thereof; and $R_2$, $R_3$, $R_4$, $R_5$, $R_6$ and $R_7$ are alkyls or silanol-terminated alkyls; and wherein n is an integer, $1 \leq n \leq 100$; and wherein the reaction is carried out at a temperature compatible with the therapeutic compound. The temperature is from about $4°$ C.$\leq T \leq 100°$ C., preferably, $5°$ C.$\leq T \leq 30°$ C., and more preferably $20°$ C.$\leq T \leq 22°$ C. In one embodiment, $R_2$, $R_3$, $R_4$, $R_5$, $R_6$ and $R_7$ are methyl groups; and $R_1$ has the structure shown in formula III, the attachment for $R_1$ indicated by an asterisk (*):

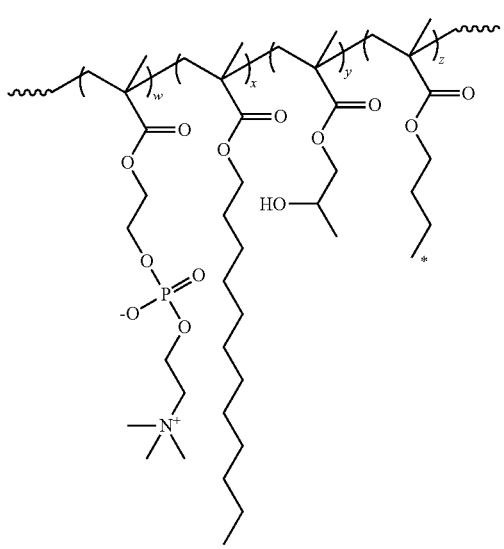

(III)

where w, x, y, and z represent the molar ratios of monomers used in the feed for preparing the polymer of formula III.

In those embodiments wherein at least one therapeutic compound is included, the compound can be, for example, sirolimus, a derivative of sirolimus, a sirolimus analog, and derivatives, esters, and salts thereof; a derivative of sirolimus includes zotarolimus. Furthermore, the at least one therapeutic compound can be an anti-proliferative agent, an anti-platelet agent, an anti-inflammatory agent, an anti-thrombotic agent and a thrombolytic agents. The composition can applied to a medical device, such as a stent; the device can be used for local or systemic drug delivery. In another embodiment, the composition has at least two therapeutic compounds, a first compound comprising zotarolimus or paclitaxel, and a second compound comprising anti-proliferative agents, anti-platelet agents, anti-inflammatory agents, anti-thrombotic agents and thrombolytic agents.

In a second aspect, the invention is directed to compositions comprising the polymers of the invention, with and without at least one therapeutic compound.

In a third aspect, the invention is directed to medical devices that include the polymers of the invention, with and without at least one therapeutic compound.

In a fourth aspect, the invention is directed specifically to a stent that includes the polymers of the invention, with and without at least one therapeutic compound.

DETAILED DESCRIPTION OF THE INVENTION

Generally, room temperature curable polymers have important applications in any situation wherein a heat labile or radiation sensitive component is desired to be incorporated into the polymer itself. Such polymers, with or without sensitive materials, are convenient and cost effective, eliminating the steps of applying heat or radiation. Room temperature curable PC polymers, specifically, have application in coating medical devices for insertion into the human body, as well as a matrix for the controlled release of therapeutic compounds. The polymers and devices coated with such polymers can be used for local as well as systemic delivery.

The present invention has numerous advantages compared to prior art techniques for curing polymers. Room temperature (RT) curing obviates the need for processing conditions (e.g., heat or γ radiation). RT cure also permits further use of the polymer coating in applications which had been previously restricted, particularly for coating devices containing more sensitive materials, such as for example nylon 11 (thermal restriction/glass transition temperature between 45-48° C.) and polytetrafluoroethylene (deterioration of mechanical properties upon exposure to γ radiation). One or more drugs can be loaded during processing to allow for a better distribution of drug throughout the bulk polymer matrix. Further more, a room temperature cure (cross-linking) also reduces or eliminates potential degradation of the PC polymer as well as the drug.

In one embodiment, the invention incorporates at least one drug as part of the composition, such that the rate of drug release, once positioned at the site of disease within the body, is dictated by the cross-link density resulting from the silanol-alkoxysilane interaction. A therapeutic amount of drug is released over a particular period at a specified rate. A phosphorylcholine-based polymer containing the alkoxysilane is a necessary component of the invention to maintain biocompatibility and hemocompatibility characteristics, preventing an inflammatory response.

Definitions

"Room temperature" typically refers to approximately 20-22° C.; however, in this application, "room temperature" (RT) refers to an incubation condition in which heat is neither added nor taken away. Accordingly, the temperature range encompassed by this term is much broader, usually indicating from about 15° C. to about 30° C. Likewise, a "reagent-compatible temperature" (RCT) is one at which the subject reagent is appreciably unchanged, after returning to RT. If a reagent is a small, denature-resistant peptide, the RCT is: 0° C.<RCT<100° C. In some instances, a reagent can lose activities at higher temperatures, but regains some or all of the activity upon returning to RT; such reagents have high RCTs.

"Pro-drug" refers to compounds which are rapidly transformed in vivo to the parent compound of the above formula, for example, by hydrolysis in blood. Thorough discussions are available (Higuchi and Stella, 1987; Roche, 1987).

"Pharmaceutically acceptable pro-drugs" refers to those pro-drugs that are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms.

"Pro-drug esters" refers to any of several ester-forming groups that are hydrolyzed under physiological conditions. Examples of pro-drug ester groups include acetyl, ethanoyl, pivaloyl, pivaloyloxymethyl, acetoxymethyl, phthalidyl, methoxymethyl, indanyl, and the like, as well as ester groups derived from the coupling of naturally or unnaturally-occurring amino acids.

"Therapeutic compound" means any reagent that when administered to a subject appropriately at an appropriate dose, has a beneficial effect on the subject. When a specific small molecule pharmaceutical is mentioned, the term includes all active derivatives. Likewise, if the therapeutic compound is a protein, ribonucleic acid (RNA) or deoxyribonucleic acid DNA), all active variants and homologous molecules are also included. The terms "therapeutic compound," "agent," "pharmacological agent," "pharmacological entity," "drug," etc., are used interchangeably.

When any substituent or variable (e.g., aryl, alkoxyl, $R_1$, $R_2$, $R_3$, $R_5$, $R_6$, etc.) occurs more than one time in a formula, such variable or substituent definition on each occurrence is independent of its definition at every other occurrence, unless otherwise indicated. Combinations of substituents and/or variables in a constituent of the compounds of the invention are permissible only if such combinations result in a stable compound.

The parenthetical nomenclature used in the definition of substituents such as $R_1$ (e.g., H, $OR_6$) is intended to reflect the substituents on all valences of the relevant atom. The invention is not limited to particular isomers and the order of moieties in the parentheses does not suggest a particular configuration.

"Acyloxy" means —OC(O)-(alkyl) and —OC(O)-(aryl).

"Alkenyl" alone or in combination, means an alkyl radical having one or more double bonds. Examples of such alkenyl radicals include ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl.

"Alkoxyl" means an alkyl group linked to oxygen.

"Alkyl," alone or in combination, means a straight-chain or branched-chain alkyl radical containing from 1 to about 22 carbon atoms, from about 1 to about 18 carbon atoms or from about 1 to about 12 carbon atoms. Examples of such radicals include methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

"Alkylcycloalkenyl" and "alkenylcycloalkenyl" mean a cycloalkenyl radical as defined above which is substituted by an alkyl or alkenyl radical as defined above. Examples of alkylcycloalkenyl and alkenylcycloalkenyl radicals include 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

"Alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

"Alkynyl" alone or in combination, means an alkyl radical having one or more triple bonds. Examples of such alkynyl groups include ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

"Amino" means —$NH_2$, —N(alkyl)2, —NH(alkyl), —N(aryl)$_2$, and —NH(aryl).

"Aralkyl" alone or in combination, means an alkyl or cycloalkyl radical as defined above in which one hydrogen atom is replaced by an aryl radical as defined above, such as benzyl, 2-phenylethyl, and the like.

"Aryl" alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

"Cycloalkenyl" alone or in combination, means a cycloalkyl radical having one or more double bonds. Examples of cycloalkenyl radicals include cyclopentenyl, cyclohexenyl, cyclooctenyl, cyclopentadienyl, cyclohexadienyl and cyclooctadienyl.

"Cycloalkenylalkyl" means an alkyl radical as defined above which is substituted by a cycloalkenyl radical as defined above. Examples of cycloalkenylalkyl radicals include 2-cyclohexen-1-ylmethyl, 1-cyclopenten-1-ylmethyl, 2-(1-cyclohexen-1-yl)ethyl, 3-(1-cyclopenten-1-yl) propyl, 1-(1-cyclohexen-1-ylmethyl)pentyl, 1-(1-cyclopenten-1-yl)hexyl, 6-(1-cyclohexen-1-1-yl)hexyl, 1-(1-cyclopenten-1-yl)nonyl and 1-(1-cyclohexen-1-yl)nonyl.

"Cycloalkyl" alone or in combination means a cycloalkyl radical containing from 3 to about 10, preferably from 3 to about 8, and most preferably from 3 to about 6, carbon atoms. Examples of such cycloalkyl radicals include cyclopropyl, cyclobutyl, cyclopentyl, cyclohexyl, cycloheptyl, cyclooctyl, and perhydronaphthyl.

"Cycloalkylalkyl" means an alkyl radical as defined above which is substituted by a cycloalkyl radical as defined above. Examples of cycloalkylalkyl radicals include cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl) methylheptyl.

"Cycloalkylcycloalkyl" means a cycloalkyl radical as defined above which is substituted by another cycloalkyl radical as defined above. Examples of cycloalkylcycloalkyl radicals include cyclohexylcyclopentyl and cyclohexylcyclohexyl.

"Halogen" includes fluoro-, chloro-, bromo- and iodo-.

"Heterocycle" includes a stable 5- to 7-membered mono- or bicyclic or stable 7- to 10-membered bicyclic heterocyclic ring that is either saturated or unsaturated and consists of carbon atoms and from one to three hetero-atoms independently selected from the group consisting of N, O and S, and wherein the nitrogen and sulfur hetero-atoms can be oxidized, and the nitrogen heteroatom can be quarternized, and including any bicyclic group in which a heterocyclic ring is fused to a benzene ring. The heterocyclic ring can be attached at any hetero-atom or carbon atom that results in a stable structure. Examples of heterocyclic elements include piperidyl, piperidinyl, pipetazinyl, pyrimidinyl, pyridazinyl, oxazolyl, furyl, and thienyl. The heterocycle can be substituted in a manner such that carbon atoms attached to a heteroatom are not directly substituted by a heteroatom, by from one to four members that can be $C_1$-$C_6$ alkyl, aryl, hydroxyl, $C_1$-$C_6$ alkoxyl, acyloxy, amino, N-acylamino, nitro and halogen.

"Heterocyclic" means ring structures containing at least one other kind of atom, in addition to carbon, in the ring. The most common of the other kinds of atoms include nitrogen, oxygen and sulfur. Examples of heterocyclics include pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

"Ketone" means —C(O)—.

"N-acylamino" means —NHC(O)-(alkyl) and —NHC(O)-(aryl).

"Nitrogen-containing heterocycle" means ring structures in which 2 carbons and a nitrogen of the ring are also part of the fifteen-membered macrocyclic ligand. The ring 10 structure can contain from about 2 to about 20 or from about 4 to about 10, carbon atoms, can be substituted or unsubstituted, partially or fully unsaturated or saturated, and can also contain nitrogen, oxygen and/or sulfur atoms in the portion of the ring which is not also part of the fifteen-membered macrocyclic ligand.

"Saturated, partially saturated or unsaturated cyclic" means fused ring structures in which 2 carbons of the ring are also part of the fifteen-membered macrocyclic ligand. The ring structure can contain from about 3 to about 20 carbon atoms or from about 5 to about 10 carbon atoms, and can also contain one or more other kinds of atoms in addition to carbon. The most common of the other kinds of atoms include nitrogen, oxygen and sulfur. The ring structure can also contain more than one ring.

"Saturated, partially saturated or unsaturated ring structure" means a ring structure in which one carbon of the ring is also part of the fifteen-membered macrocyclic ligand. The ring structure can contain from about 3 to about 20 or from about 5 to about 10, carbon atoms and can also contain nitrogen, oxygen and/or sulfur atoms.

Practicing the Invention

In the methods of the invention, a molecule having a formula of I:

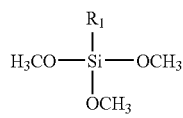

(I)

wherein $R_1$ is a polymer, the polymer containing an acyloxy, alkenyl, alkoxyl, alkyl, alkylcycloalkenyl, alkylcycloalkyl, alkenylcycloalkyl, alkynyl, amino, aralkyl, aryl, cycloalkenyl, cycloalkenylalkyl, cycloalkyl, cycloalkylalkyl, cycloalkylcycloalkyl, halogen, heterocycle, heterocyclic, ketone, N-acylamino, N-containing heterocycle; saturated cyclic, partially saturated cyclic or unsaturated cyclic; saturated, partially saturated or unsaturated ring structure, or combinations thereof, is reacted with a molecule having a formula II:

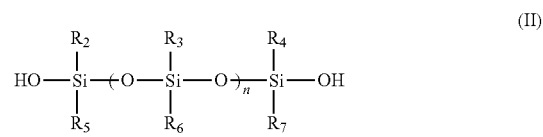

(II)

wherein $R_2$, $R_3$, $R_4$, $R_5$, $R_6$ and $R_7$ are alkyls or silanol-terminated alkyls; n represent any integer of 1-100. In a preferred embodiment, $R_2$, $R_3$, $R_4$, $R_5$, $R_6$ and $R_7$ are methyl groups, and $R_1$ has the structure shown in formula III, the attachment for $R_1$ being indicated by an asterisk (*):

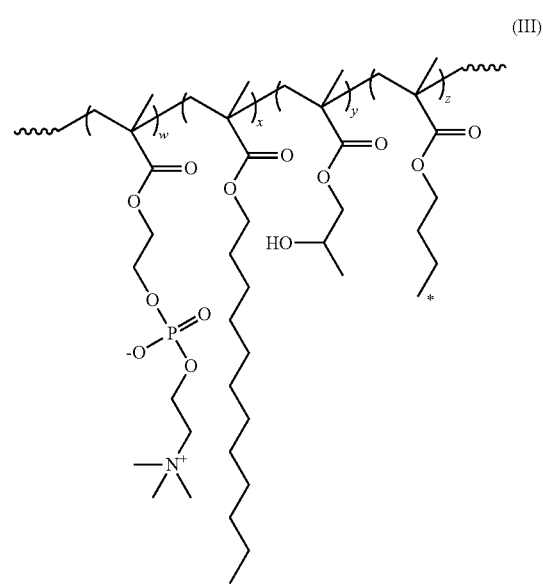

(III)

where w, x, y, and z represent the molar ratios of monomers used in the feed for preparing the polymer of formula III, resulting in a molecule represented by formula IV:

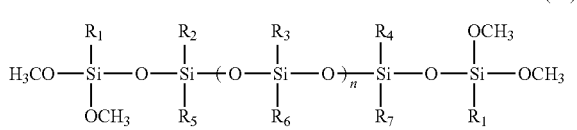

(IV)

Thus, in a most preferred embodiment, the invention encompasses the reaction shown in Scheme 1, where a molecule of formula V is reacted with a molecule of formula VI to create a polymer product of formula VII and a by-product of formula VIII:

SCHEME 1
Room temperature polymerization scheme using a PC polymer
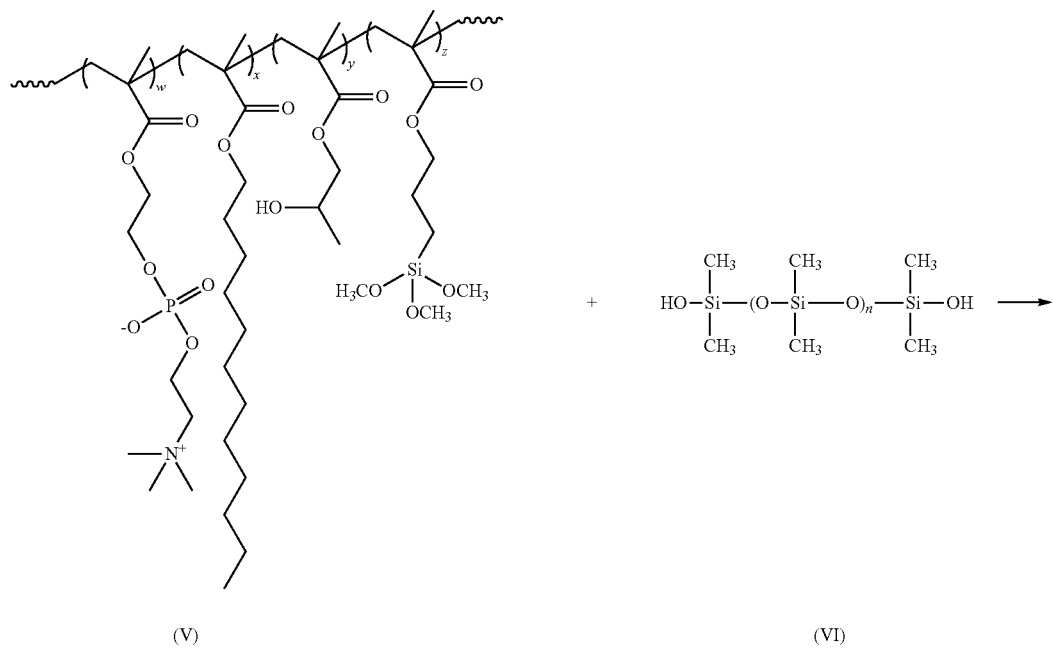
(V)  (VI)
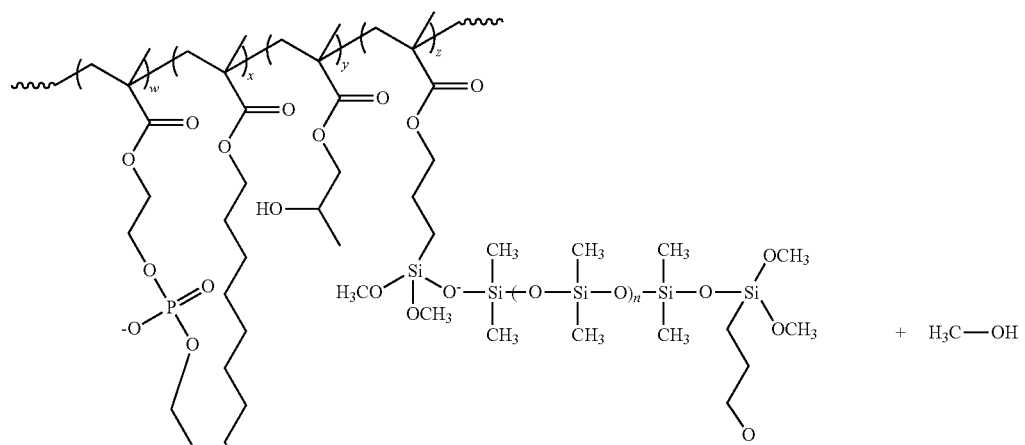

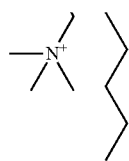
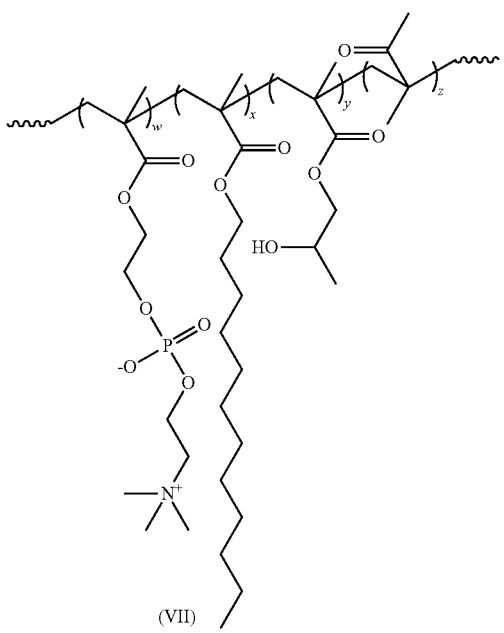

(VII)  (VIII)

The polymer product of the reaction shown in Scheme 1 is useful for coating, for example, medical devices. Furthermore, the product finds use in incorporating therapeutic compounds such that medical devices are then coated with the compounds. Preferred polymer/therapeutic compound combinations include zotarolimus, zotarolimus and dexamethasone, zotarolimus and paclitaxel, zotarolimus and other therapeutic compounds, and paclitaxel and other therapeutic compounds.

In general, the methods of the invention can be practiced as follows: the siloxane-terminated polymer of choice (shown by the general structure of formula I), such as phosphorylcholine polymer PC1036 (Biocompatibles Ltd., Farnham, Surrey, UK), is dissolved in an appropriate solvent, such as dichloromethane (DCM). After the polymer is dissolved, a hydroxy-terminated siloxane (shown by the general structure of formula II), such as hydroxy-terminated polydimethylsiloxane (HTPDMS; available from Sigma-Aldrich; Saint Louis, Mo.), is added. The solution is then mixed, and then applied to a surface, a device, or other instrumentality, and allowed to cure. In the case of PC1036 and HTPDMS, curing is often apparent within 2 minutes of incubation. Although a preferred embodiment is described herein, the order of adding the reactants to the solution does not matter.

Alternatively, solutions of the reactants can be made and then added together. Thus a solution of the siloxane-terminated polymer is made, and then is mixed with a solution containing the second reactant, a hydroxy-terminated siloxane, creating a third solution; this third solution is then used to coat the object of choice, for example.

Incorporating a Therapeutic Compound into the Polymer

Because of the advantages of the invention, therapeutic compounds that would otherwise be sensitive to polymerization conditions (e.g., applied heat extremes, γ-irradiation), can be incorporated into the polymers. Such incorporation is advantageous because the degree of cross-linking can be controlled, which in turn affects the release rate of the therapeutic. In its simplest form, the therapeutic is added to the reaction mixture as it proceeds, in one or more of the reactant mixtures in the case where separate solutions of the reactants are prepared before mixing, or as a third solution added during polymerization.

Medical Devices and Therapeutic Compound-containing Polymers (TCCPs)

Because of the methods of producing the polymers of the invention are gentle, they are exceptionally useful for incorporating therapeutic compounds for delivery via a polymer-coated, or polymer, device.

For example, compounds incorporated into the polymerization reaction can be applied to medical devices, such as stents. Incorporation of a compound into the polymeric coating of the stent can be carried out by dipping the stent into a solution containing the compound in a polymer solution for a sufficient period of time (such as, for example, five minutes) and then drying the coated stent, preferably by air, for a sufficient period of time (such as, for example, 30 minutes). Other methods of applying the TCCP solution can be used, such as spraying. In addition to stents, other devices can be used to introduce therapeutic compounds cast with the polymers of this invention, including grafts, catheters, and balloons or other interventional devices. In some cases, the therapeutic compound is applied to the device before or after the polymer solution, although co-coating is preferred.

Therapeutic Compounds

Polymer-coated stents can be coated with almost any reagent. By way of example, not meant to limit the invention in anyway, a stent coated with the polymers of the invention or by the methods of the invention can be used in the treatment of restenosis—the phenomenon of re-narrowing of blood vessels after repairing the original stenotic lesion.

When the medical device is a stent, and the condition to be treated is restenosis, the therapeutic compounds that can be incorporated into the polymers of the invention are those that aid in the prevention of restenosis. A particularly useful therapeutic compound, preferred, are tetrazole-containing analogues of sirolimus (rapamycin), such as that discovered by Mollison et al. (Mollison, 2000).

In general, these compounds can be classified into the categories of anti-proliferative agents, anti-platelet agents, anti-inflammatory agents, anti-thrombotic agents, thrombolytic agents and other agents known in the art. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

A highly preferred anti-mitotic is paclitaxel. Paclitaxel includes the alkaloid itself and naturally occurring forms and derivatives, as well as synthetic and semi-synthetic forms.

Anti-platelet agents act by (1) inhibiting adhesion of platelets to a surface, typically a thrombogenic surface, (2) inhibiting aggregation of platelets, (3) inhibiting activation of platelets, or (4) a combination of these activities. Anti-platelet agents that act as inhibitors of adhesion of platelets include eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, peptides that block P-selectin or E-selectin binding to their respective ligands, saratin, and anti-von Willebrand factor antibodies. Agents that inhibit ADP-mediated platelet aggregation include disagregin and cilostazol.

Anti-inflammatory agents can also be used. Examples of these include prednisone, dexamethasone, hydrocortisone, estradiol, and non-steroidal anti-inflammatories, such as acetaminophen, ibuprofen, naproxen, fluticasone, clobetasol, adalimumab and sulindac. Other anti-inflammatory agents inhibit binding of cytokines or chemokines to cognate receptors. Examples of these include anti-interleukin (IL)-1, anti-IL2, anti-IL3, anti-IL4, anti-IL8, anti-IL15, anti-MCP1, anti-GM-CSF, and anti-TNF antibodies.

Anti-thrombotic agents include chemical and biological agents that can intervene at any stage in the coagulation pathway. Examples include small molecules that inhibit the activity of factor Xa. In addition, heparinoid-type agents that can inhibit both FXa and thrombin, either directly or indirectly, such as, for example, heparin, heparan sulfate, low molecular weight heparins, such as, for example, Clivarin®, and synthetic oligosaccharides, such as, for example, Arixtra®. Also included are direct thrombin inhibitors, such as melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors; for example, anti-factor VII/VIIa antibodies, rNAPc2, and tissue factor pathway inhibitor (TFPI).

Thrombolytic agents help degrade thrombi (clots) and can also be used as adjunctive agents, because lysing a clot helps to disperse platelets trapped within the fibrin matrix of a thrombus. Representative examples of thrombolytic agents include urokinase or recombinant urokinase, pro-urokinase or recombinant pro-urokinase, tissue plasminogen activator or its recombinant form, and streptokinase.

Other therapeutic compounds that can be used in the invention include cytotoxic drugs, such as apoptosis inducers, including transforming growth factor (TGF), and topoisomerase inhibitors, such as, 10-hydroxycamptothecin, irinotecan, and doxorubicin. Drugs that inhibit cell de-differentiation and cytostatic drugs can also be used.

Other agents useful agents in the treatment of restenosis prevention include anti-lipaedemic agents, such as, for example, fenofibrate, matrix metalloproteinase inhibitors, such as, for example, batimistat, antagonists of the endothelin-A receptor, such as, for example, darusentan, and antagonists of the $\alpha v\beta 3$ integrin receptor.

One or more of such agents in combination with each other can be delivered from polymers according to the present invention.

Other conditions that can be treated using a stent or other medical device to deliver therapeutic compounds and the polymers of the invention include ischemic bowel diseases, inflammatory bowel diseases, necrotizing enterocolitis, intestinal inflammations/allergies such as Coeliac diseases, proctitis, eosinophilic gastroenteritis, mastocytosis, Crohn's disease and ulcerative colitis; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) that occurs upon preservation, transplantation or ischemic disease (for example, thrombosis and cardiac infarction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenesis, metastasis of carcinoma and hypobaropathy; diseases caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as autoimmune hepatitis, primary biliary cirrhosis and sclerosing cholangitis), partial liver resection, acute liver necrosis (e.g., necrosis caused by toxin, viral hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, cytomegalovirus infection, particularly HCMV infection, anti-inflammatory activity, sclerosing and fibrotic diseases such as nephrosis, scleroderma, pulmonary fibrosis, arteriosclerosis, congestive heart failure, ventricular hypertrophy, post-surgical adhesions and scarring, stroke, myocardial infarction and injury associated with ischemia and reperfusion, and the like.

Additionally, compounds having FK-506 antagonistic properties can be used. These compounds can be used in the treatment of immunodepression or a disorder involving immunodepression. Examples of disorders involving immunodepression include acquired immune deficiency syndrome, cancer, fungal infections, senile dementia, trauma (including wound healing, surgery and shock), chronic bacterial infection, and central nervous system disorders.

A therapeutically effective amount of a therapeutic compound can be administered in pure form or as a pharmaceutically acceptable salt, ester or prodrug form. Alternatively, compounds are administered as pharmaceutical compositions containing the compound of interest in combination with one or more pharmaceutically acceptable excipient or other beneficial agent. "Therapeutically effective amount" of a pharmaceutical substance means a sufficient amount of the substance to treat disorders, at a reasonable benefit/risk ratio applicable to any medical treatment. It will be understood, however, that the total daily usage of the compounds and the methods of administering the compounds which have been incorporated into the polymers of the invention, is decided by on having sound medical judgment, such as a physician. The specific therapeutically effective dose level for any particular patient depends upon a variety of factors including: the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of pharmacological agents administered to a subject generally ranges from about 0.01 to about 10 mg/kg/day. The daily dose from a stent depends in part on the length of the stent and the degree of cross-linking of the polymers. For example, a 15 mm coronary stent can contain a drug in an amount ranging from about 1 to about 120 micrograms and can deliver that drug within several hours to several weeks, or longer. If desired, the effective daily dose can be divided into multiple doses; consequently, single-dose compositions contain such amounts or sub-multiples thereof to make up the daily dose.

Therapeutic Compounds and Polymers

The choice of polymer depends in part on the therapeutic compound or agents desired to be incorporated into the polymer; i.e., the drug, is substantially soluble. A purpose of the coating is to serve as a controlled release vehicle for the therapeutic compound(s) or as a reservoir for a therapeutic compound(s) to be delivered at the site of a lesion, remote from the location of the device implant or systemically. The coating can be polymeric and can further be hydrophilic, hydrophobic, biodegradable, or non-biodegradable. With the caveat that the polymers formed by the methods of the invention terminate with at least one siloxane group, the polymers can be in part polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyorthoesters, polyanhydrides, polycarbonates, polypropylenes, polylactic acids, polyglycolic acids, polycaprolactones, polyhydroxybutyrate valerates, polyacrylamides, polyethers, and mixtures and copolymers of the foregoing. These polymers can be modified to terminate with at least one siloxane group using methods known to those of skill in the art. Coatings prepared from polymeric dispersions such as polyurethane dispersions (BAYHYDROL, etc.) and acrylic acid latex dispersions can also be used.

Biodegradable polymers that can be used in this invention include polymers such as poly(L-lactic acid), poly(DL-lactic acid), polycaprolactone, poly(hydroxy butyrate), polyglycolide, poly(diaxanone), poly(hydroxy valerate), polyorthoester; copolymers such as poly(lactide-co-glycolide), polyhydroxy(butyrate-co-valerate), polyglycolide-co-trimethylene carbonate; polyanhydrides; polyphosphoester; polyphosphoester-urethane; polyamino acids; polycyanoacrylates; biomolecules such as fibrin, fibrinogen, cellulose, starch, collagen and hyaluronic acid; and mixtures of the foregoing. Those that do not terminate with at least one siloxane group can be modified according to methods known to those of skill in the art.

Biostable materials that are also suitable include polymers such as polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (such as styrene acrylonitrile copolymers, ethylene methyl methacrylate copolymers, ethylene vinyl acetate), polyethers, rayons, cellulosics (such as cellulose acetate, cellulose nitrate, cellulose propionate, etc.), parylene and derivatives thereof; and mixtures and copolymers of the foregoing. Those that do not terminate with at least one siloxane group can be modified according to methods known to those of skill in the art.

Pharmaceutical Compositions

The polymers of the invention can be used to administer therapeutic compounds, with a pharmaceutically acceptable carrier or recipient if necessary. These can be administered orally, rectally, parenterally, intracisternally, intravaginally, intraperitoneally, topically (as by powders, ointments, drops or transdermal patch), bucally, as an oral or nasal spray, or locally, as in a stent placed within the vasculature. "Pharmaceutically acceptable carrier" means a non-toxic solid, semi-solid or liquid filler, diluent, encapsulating material or formulation auxiliary of any type. "Parenteral" refers to modes of administration that include intravenous, intra-arterial, intramuscular, intraperitoneal, intrasternal, subcutaneous and intra-articular injection, infusion, and placement, such as, for example, in vasculature.

Pharmaceutical compositions of this invention for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. Isotonic agents, such as sugars, sodium chloride, and the like, can be included. Prolonged absorption of the injectable pharmaceutical form may be brought about by the inclusion of agents that delay absorption such as aluminum monostearate and gelatin.

In some cases, in order to prolong the effect of the drug, it is desirable to slow the absorption of the drug from, for example, subcutaneous or intramuscular injection. This can be accomplished using a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable forms can be made by forming microencapsule matrices of the drug in biodegradable polymers such as poly-lactide-polyglycolide. Depending upon the ratio of drug to polymer and the nature of the particular polymer used, the rate of drug release can be controlled. Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

The active compounds can also be in micro-encapsulated form, if appropriate, with one or more of the above-mentioned excipients.

Polymer Layers and Therapeutic Compounds on Medical Devices

There is much flexibility in providing suitable drug-loaded polymer layers. For example, within therapeutic window parameters (generally levels between therapeutically effective and toxicity) associated with the drugs of interest, ratios of the drugs used in combination can be varied relative to each other. For example, one embodiment has a 90:10 total drug: polymer ratio with where the ratio of drugs in the combination can be 1:1. Upper limits on the total amount of drug will depend on several factors, including miscibility of the selected drugs in the selected polymer, the stability of the drug/polymer mixture, e.g., compatibility with sterilization, and the physical properties of the mixture, e.g., flowability/processability, elasticity, brittleness, viscosity (does not web or bridge between stent struts), coating thickness that adds substantially to the stent profile or causes delamination or cracking or is difficult to crimp.

Overcoat thickness (if an overcoat is used) desirably should not excessively impede release kinetics of the drugs.

EXAMPLES

The following examples illustrate the concept of a room temperature cure for siloxane-terminated polymers. In these examples, a phosphorylcholine polymer is used to illustrate the methods of the invention, in combination with a hydroxy-terminated polydimethylsiloxane, including the addition of a drug.

Example 1

Room Temperature Cure of a Phosphorylcholine Polymer with a Hydroxy-Terminated Polydimethylsiloxane In this example, a phosphorylcholine polymer was dissolved in a solvent, and then reacted with a hydroxy-terminated siloxane. After mixing, the solution was incubated at room temperature and exposed to air.

Into a 40-ml scintillation vial was added 1.004 grams of phosphorylcholine polymer PC1036 (Biocompatibles Ltd., Farnham, Surrey, UK), followed by 10 ml dichloromethane (DCM). The mixture was mixed using a vortex and swirled until the polymer was completely dissolved (~20 min.). To this solution was added 0.012 grams hydroxy-terminated polydimethylsiloxane (HTPDMS; available from Sigma-Aldrich; Saint Louis, Mo.). The mixture was mixed using a vortex and swirled until the HTPDMS was dissolved. The clear, water-white solution was poured into an aluminum weighing dish and allowed to cure, open to the air. A thin, tough film on the surface of the solution ("skin-over") was apparent within 2 minutes.

Example 2

Room Temperature Cure of a Phosphorylcholine Polymer with Hydroxy-terminated Polydimethylsiloxane This example is similar to Example 1 with the order of the reactants changed; that is, the hydroxy-terminated siloxane was first added to solution, followed by addition of the phosphorylcholine polymer.

Into a 40-ml scintillation vial was added 0.290 gram HTPDMS followed by 10 ml DCM. The mixture was mixed with a vortex and swirled until the HTPDMS was completely dissolved. To this solution was added 1.000 gram PC1036. The mixture was mixed with a vortex and swirled until the polymer was completely dissolved (about 20-30 min.). The cloudy solution was poured into an aluminum weighing dish and allowed to cure, open to the air. Skin-over was observed within 2 minutes.

Example 3

Room Temperature-cure of a Phosphorylcholine Polymer with a Hydroxy-terminated Polydimethylsiloxane In this example, a first solution containing only PC1036 was mixed; a second solution containing only HTPDMS was made, and then the two solutions were admixed immediately before coating a device by dipping into the resulting solution. The coating on the device then cured, as evidenced by visible inspection.

Solution A: Into a 40 ml scintillation vial was added 1.011 gram PC1036 followed by 5 ml DCM. The mixture was mixed using a vortex and swirled until the PC1036 was completely dissolved, about 2 hours.

Solution B: Into a 40-ml scintillation vial was added 0.157 gram HTPDMS followed by 5 ml DCM. The mixture was mixed using a vortex and swirled until the polymer was completely dissolved, about 2-3 minutes.

The contents of Solution B was poured into Solution A and the mixture was agitated using a vortex and swirled, creating a coating solution, Solution C.

A 1-cm diameter, stainless steel coupon, rinsed with ethanol, was attached to a hemostat and dipped into the Solution C for 5 seconds, allowing the top of the coupon to be fully covered with solution. Upon exposure to air, cure was apparent within 1 minute.

The remainder of the solution was poured into an aluminum weighing dish and allowed to cure, open to the air. Skin-over was apparent within 2 minutes.

Example 4

Room Temperature Cure of a Phosphorylcholine Polymer with a Hydroxy-terminated Polydimethylsiloxane and Addition of a Drug This example involved the room-temperature cure of PC1036 polymer with HTPDMS and a drug, dexamethasone.

Into a 40-ml scintillation vial was added 1.00685 grams PC1036 polymer followed by 10 ml DCM. The mixture was swirled periodically until the polymer was completely dissolved, about 2 hours. After the polymer was dissolved, 5.83 grams dexamethasone was added. The mixture was swirled to dissolve the drug. Once dissolved, as evidenced by a clear solution, 0.176 grams HTPDMS was added and the mixture and swirled vigorously. Approximately 3 ml of the resulting solution was poured into an aluminum weighing dish and exposed to air at room temperature. The remaining solution was poured into a new aluminum weighing dish and exposed to air at room temperature. In both cases, skin-over was observed within 2 minutes.

REFERENCES

Bowers, R., S. Jones, and P. Stratford. U.S. Pat. No. 5,648,442. 1997. Polymeric surface coatings.

Bowers, R., S. Jones, and P. Stratford. U.S. Pat. No. 6,090,901. 2000. Polymeric surface coatings.

Bowers, R., S. Jones, and P. Stratford. U.S. Pat. No. 6,284,854. 2001. Polymeric surface coatings.

Bowers, R., S. Jones, P. Stratford, and S. Charles. U.S. Pat. No. 5,705,583. 1998. Polymeric surface coatings.

Hernandez, P. European Patent Application Publication 0 604 851. 1994. Alkoxysilane functionalized acrylic polymer composition.

Higuchi, T., and V. Stella. 1987. Pro-drugs as Novel Delivery systems.

Lewis, A. L., Z. L. Cumming, H. H. Goreish, L. C. Kirkwood, L. A. Tolhurst, and P. W. Stratford. 2001. Crosslinkable coatings from phosphorylcholine-based polymers. Biomaterials. 22:99-111.

Lewis, A. L., P. D. Hughes, L. C. Kirkwood, S. W. Leppard, R. P. Redman, L. A. Tolhurst, and P. W. Stratford. 2000. Synthesis and characterisation of phosphorylcholine-based polymers useful for coating blood filtration devices. Biomaterials. 21:1847-59.

Mollison, K. U.S. Pat. No. 6,015,815. 2000. Tetrazole-containing sirolimus analogs with shortened half-lives.

Roche, E. 1987. Bioreversible Carriers in Drug Design. American Pharmaceutical Association and Pergamon Press.

We claim:

1. A method of preparing a composition, said composition comprising at least one therapeutic compound and a molecule of formula IV:

$$H_3CO-\underset{\underset{OCH_3}{|}}{\overset{\overset{R_1}{|}}{Si}}-O-\underset{\underset{OCH_3}{|}}{\overset{\overset{R_2}{|}}{Si}}-(O-\underset{\underset{R_6}{|}}{\overset{\overset{R_3}{|}}{Si}}-O)_n-\underset{\underset{R_7}{|}}{\overset{\overset{R_4}{|}}{Si}}-O-\underset{\underset{R_1}{|}}{\overset{\overset{OCH_3}{|}}{Si}}-OCH_3 \quad (IV)$$

said method comprising reacting a molecule of formula I:

$$H_3CO-\underset{\underset{OCH_3}{|}}{\overset{\overset{R_1}{|}}{Si}}-OCH_3 \quad (I)$$

in situ with a molecule of formula II:

$$HO-\underset{\underset{R_5}{|}}{\overset{\overset{R_2}{|}}{Si}}-(O-\underset{\underset{R_6}{|}}{\overset{\overset{R_3}{|}}{Si}}-O)_n-\underset{\underset{R_7}{|}}{\overset{\overset{R_4}{|}}{Si}}-OH \quad (II)$$

adding the therapeutic compound to reactant (I) or reactant (II) or both prior to the reaction thereof, or adding the therapeutic compound to the reaction mixture of the reactants during the reaction thereof; wherein $R_1$ comprises a polymer, the polymer containing at least one group selected from the group consisting of an acyloxy, alkenyl, alkoxyl, alkyl, alkylcycloalkenyl, alkylcycloalky, alkenylcycloalkyl, alkynyl, amino, aralkyl, aryl, cycloalkenyl, cycloalkenylalkyl, cycloalkyl, cycloalkylalkyl, cycloalkylcycloalkyl, halogen, heterocycle, heterocyclic, ketone, N-acylamino, N-containing heterocycle; and combinations thereof; and $R_2$, $R_3$, $R_4$, $R_5$, $R_6$ and $R_7$ are alkyls or silanol-terminated alkyls; and wherein n is an integer, $1 \leq n \leq 100$; and wherein the reaction is carried out at a temperature compatible with the therapeutic compound.

2. The method of claim 1, wherein the temperature, T, at which the reaction is carried out is $4°\ C. < T \leq 100°\ C.$ 3. The method of claim 2, wherein $15°\ C. \leq T \leq 30°\ C.$ 4. The method of claim 2, wherein $20°\ C. \leq T \leq 22°\ C.$ 5. The method of claim 1, wherein the therapeutic compound is one selected from the group consisting of sirolimus, zotarolimus, esters, and salts thereof.

6. The method of claim 5, wherein the therapeutic compound comprises zotarolimus.

7. The method of claim 1, wherein the therapeutic compound comprises one selected from the group consisting of anti-proliferative agents, anti-platelet agents, anti-inflammatory agents, anti-thrombotic agents and thrombolytic agents.

8. The method of claim 7, wherein the anti-inflammatory agent is one selected from the group consisting of dexamethasone, hydrocortisone, estradiol, acetaminophen, ibuprofen, naproxen, fluticasone, clobetasol, adalimumab and sulindac.

9. The method of claim 1, wherein the therapeutic compound comprises an antibody.

10. The method of claim 7, wherein the therapeutic compound comprises dexamethasone.

11. The method of claim 1, further comprising applying the polymer to a medical device.

12. The method of claim 11, wherein the medical device comprises a stent.

13. The method of claim 1, wherein the composition comprising at least two therapeutic compounds, a first compound comprising zotarolimus or paclitaxel, and a second compound selected from the group consisting of anti-proliferative agents, anti-platelet agents, anti-inflammatory agents, anti-thrombotic agents and thrombolytic agents.

14. A method of preparing a composition, said composition comprising at least one therapeutic compound and a molecule of formula IX:

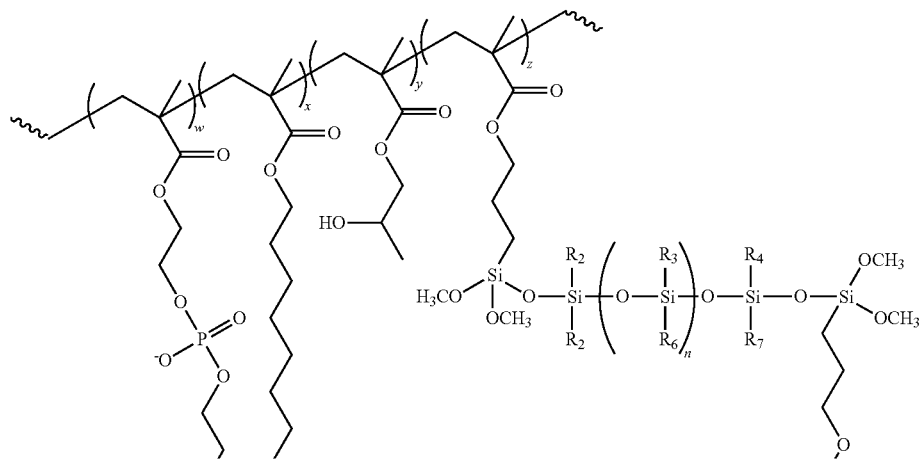

(IX)

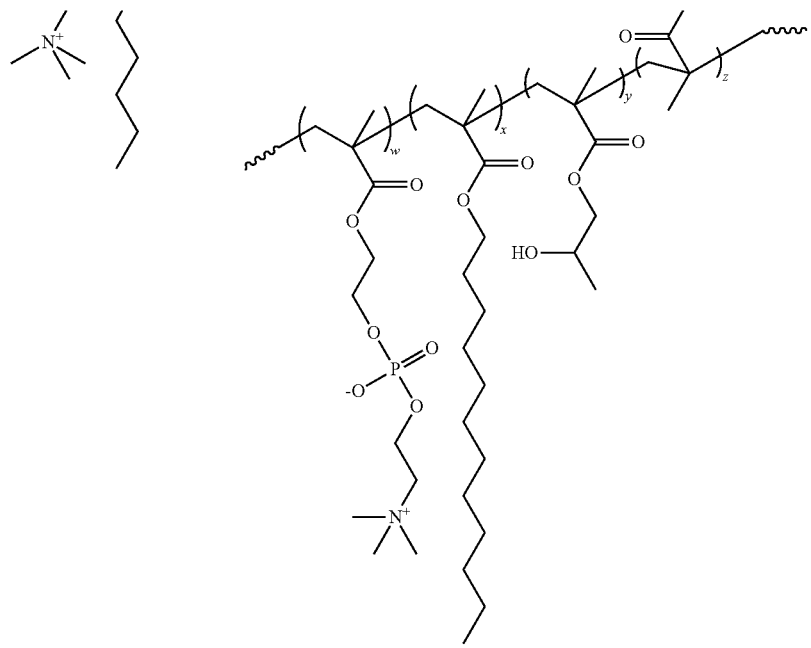

said method comprising reacting a molecule of formula V:

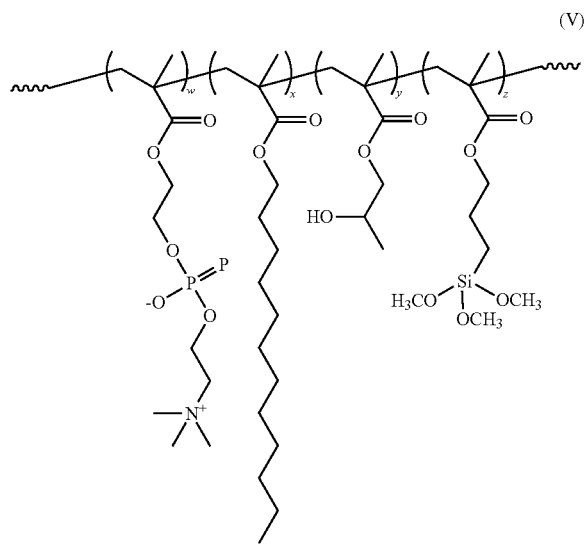

(V)

in situ with a molecule of formula II:

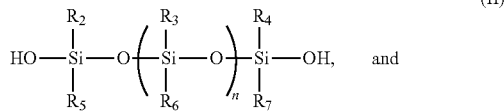

(II)

adding the therapeutic compound to reactant (V) or reactant (II) or both prior to the reaction thereof, or adding the therapeutic compound to the reaction mixture of the reactants during the reaction thereof;

wherein n is an integer, $1 \leq n \leq 100$; where w, x, y, and z represent the molar ratios of monomer used in the feed for preparing the polymer of formula V;

$R_2$, $R_3$, $R_4$, $R_5$, $R_6$ and $R_7$ are alkyls or alkyl-terminated silanols; and wherein the reaction is carried out at a temperature compatible with the therapeutic compound.

15. The method of claim 14, wherein the temperature, T, at which the reaction is carried out is $4° C. \leq T \leq 100° C.$ 16. The method of claim 15, wherein $15° C. \leq T \leq 30° C.$ 17. The method of claim 14, wherein $20° C. \leq T \leq 22° C.$ 18. The method of claim 14, wherein the therapeutic compound is one selected from the group consisting of sirolimus, zotarolimus, esters, and salts thereof.

19. The method of claim 18, wherein the therapeutic compound comprises zotarolimus.

20. The method of claim 14, wherein the therapeutic compound comprises one selected from the group consisting of anti-proliferative agents, anti-platelet agents, anti-inflammatory agents, anti-thrombotic agents and thrombylytic agents.

21. The method of claim 20, wherein the anti-inflammatory agent is one selected from the group consisting of dexamethasone, hydrocortisone, estradiol, acetaminophen, ibuprofen, naproxen, fluticasone, clobetasol, adalimumab and sulindac.

22. The method of claim 14, wherein the therapeutic compound comprises an antibody.

23. The method of claim 20, wherein the therapeutic compound comprises dexamethasone.

24. The method of claim 14, further comprising applying the polymer to a medical device.

25. The method of claim 24, wherein the medical device comprises a stent.

26. The method of claim 14, wherein the composition comprising at least two therapeutic compounds, a first compound comprising zotarolimus or paclitaxel, and a second compound selected from the group consisting of anti-proliferative agents, anti-platelet agents, anti-inflammatory agents, anti-thrombotic agents and thrombolytic agents.

27. The method of claim 14, wherein $R_2$, $R_3$, $R_4$, $R_5$, $R_6$ and $R_7$ are methyl groups.

28. A method of preparing a composition, said composition comprising at least one therapeutic compound and a molecule of formula VII

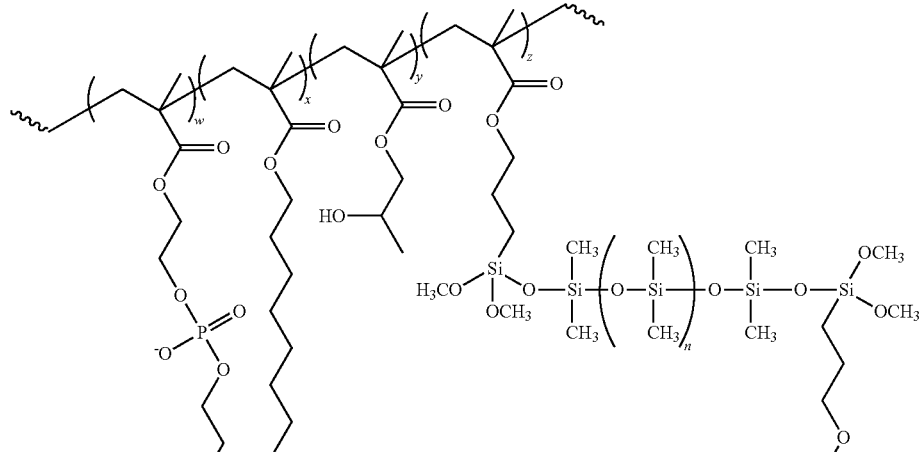

(VII)

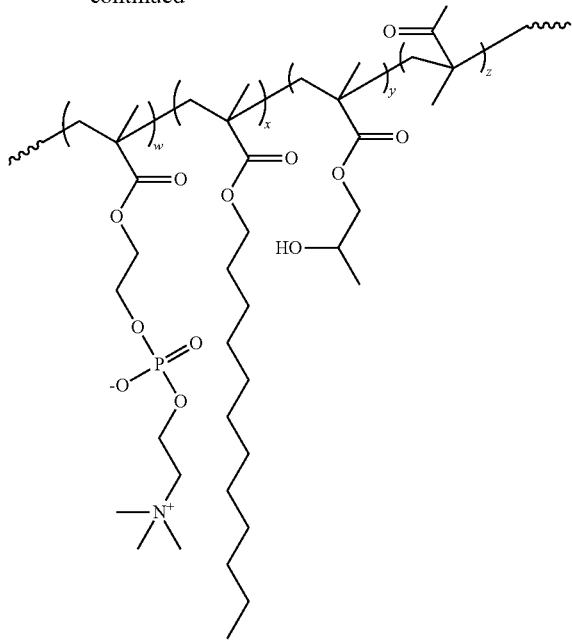

said method comprising reacting a molecule of formula V:

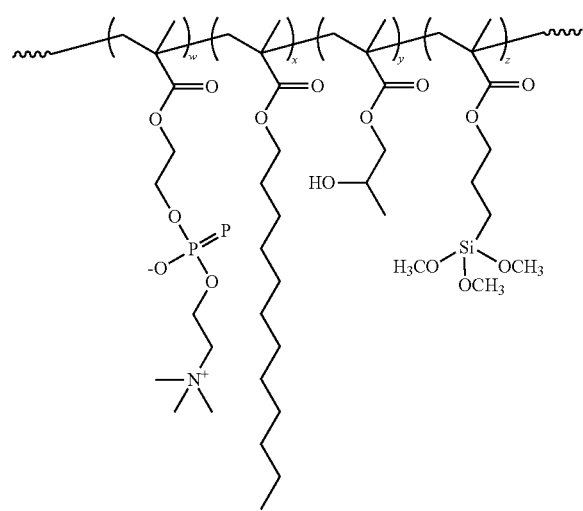

(V)

in situ with a molecule of formula VI:

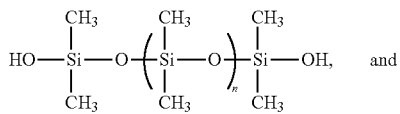

(VI)

adding the therapeutic compound to reactant (V) or reactant (VI) or both prior to the reaction thereof, or adding the therapeutic compound to the reaction mixture of the reactants during the reaction thereof;

wherein n is an integer, $1 \leq n \leq 100$;

where w, x, y, and z represent the molar ratios of monomers used in the feed for preparing the polymer of formula VI; and wherein the reaction is carried out at a temperature compatible, with the therapeutic compound.

29. The method of claim 28, wherein the temperature, T, at which the reaction is carried out is $4°$ C.$\leq$T$\leq$100° C.

30. The method of claim 29, wherein 15° C.$\leq$T$\leq$30° C.

31. The method of claim 29, wherein 20° C.$\leq$T$\leq$22° C.

32. The method of claim 28, wherein the therapeutic compound is one selected from the group consisting of sirolimus, zotarolimus, and derivatives, esters, and salts thereof.

33. The method of claim 32, wherein the therapeutic compound comprises zotarolimus.

34. The method of claim 28, wherein the therapeutic compound comprises one selected from the group consisting of anti-proliferative agents, anti-platelet agents, anti-inflammatory agents, anti-thrombotic agents and thrombylytic agents.

35. The method of claim 34, wherein the anti-inflammatory agent is one selected from the group consisting of dexamethasone, hydrocortisone, estradiol, acetaminophen, ibuprofen, naproxen, fluticasone, clobetasol, adalimumab and sulindac.

36. The method of claim 28, wherein the therapeutic compound comprises an antibody.

37. The method of claim 34, wherein the therapeutic compound comprises dexamethasone.

38. The method of claim 28, further comprising applying the polymer to a medical device.

39. The method of claim 38, wherein the medical device comprises a stent.

40. A composition made by any of claims 1, 14 and 28.

41. A medical device comprising a composition made by any of claims 1, 14 and 28.

42. A stent comprising a composition made by any of claims 1, 14 and 28.

* * * * *